United States Patent [19]
Anderson

[11] Patent Number: 5,891,059
[45] Date of Patent: Apr. 6, 1999

[54] METHOD FOR DETECTING EDEMA

[75] Inventor: Jared Arnold Anderson, Woodside, Calif.

[73] Assignee: Mr. Jared Arnold Anderson, Woodside, Calif.

[21] Appl. No.: 958,818

[22] Filed: Oct. 28, 1997

[51] Int. Cl.$^6$ .................................................. A61B 5/103
[52] U.S. Cl. ........................ 600/587; 600/561; 600/595
[58] Field of Search ................................. 600/561, 587, 600/592, 595

[56] References Cited

U.S. PATENT DOCUMENTS

| | | | |
|---|---|---|---|
| 4,606,353 | 8/1986 | Timm ...................................... | 600/587 |
| 4,700,715 | 10/1987 | Levine et a.l ........................... | 600/587 |
| 4,735,195 | 4/1988 | Blum et al. .............................. | 601/33 |
| 4,766,909 | 8/1988 | Timm et al. ............................. | 600/587 |
| 4,817,625 | 4/1989 | Miles ....................................... | 600/595 |
| 4,848,361 | 7/1989 | Penney et al. .......................... | 600/595 |
| 5,437,610 | 8/1995 | Cariapa et al. ......................... | 601/152 |

OTHER PUBLICATIONS

Lindahl, O.A. et al., "Impression Technique For The Assessment Of Oedema: Comparison With A New Tactile Sensor That Measures Physical Properties Of Tissue," *Medical & Biological Engineering & Computing* (1995) vol. 33:27–32.

Dramaix, M. et al., "Serum Albumin Concentration, Arm Circumference, and Odema and Subsequent Risk of Dying In Children In Central Africa," *BMJ* (1993) vol. 307:710–713.

Boland, R. et al., "Development and Evaluation of a Precision Forearm and Hand Volunteer and Measuring Cylinder," *J Hand Ther* (1996) vol. 9 (4):349–358.

*Primary Examiner*—Max Hindenburg
*Assistant Examiner*—Charles Marmor, II
*Attorney, Agent, or Firm*—Bozicevic & Reed LLP; Bret E. Field

[57] ABSTRACT

Methods and devices are provided for detecting the presence of edema in a mammalian host. In the subject methods, the perimeter of at least one limbic extremity, preferably a lower limbic extremity such as an ankle or foot, is measured to obtain a perimeter value. The perimeter value is then compared to a control value and any difference is identified. The difference is then related to the presence of edema in the patient. The subject methods find use in the diagnosis and management of diseases characterized by the presence of edema as a physical manifestation, particularly congestive heart failure, more particularly right-sided or biventricular failure.

17 Claims, 3 Drawing Sheets

INDEX POST USED TO CREATE REVERSE CURVE

INDEX POST    ATTACHMENT CAN BE MADE TO CABEL ITSELF OR TO POST

PREF. EMBODIMENT USES TWO MEASUREMENTS

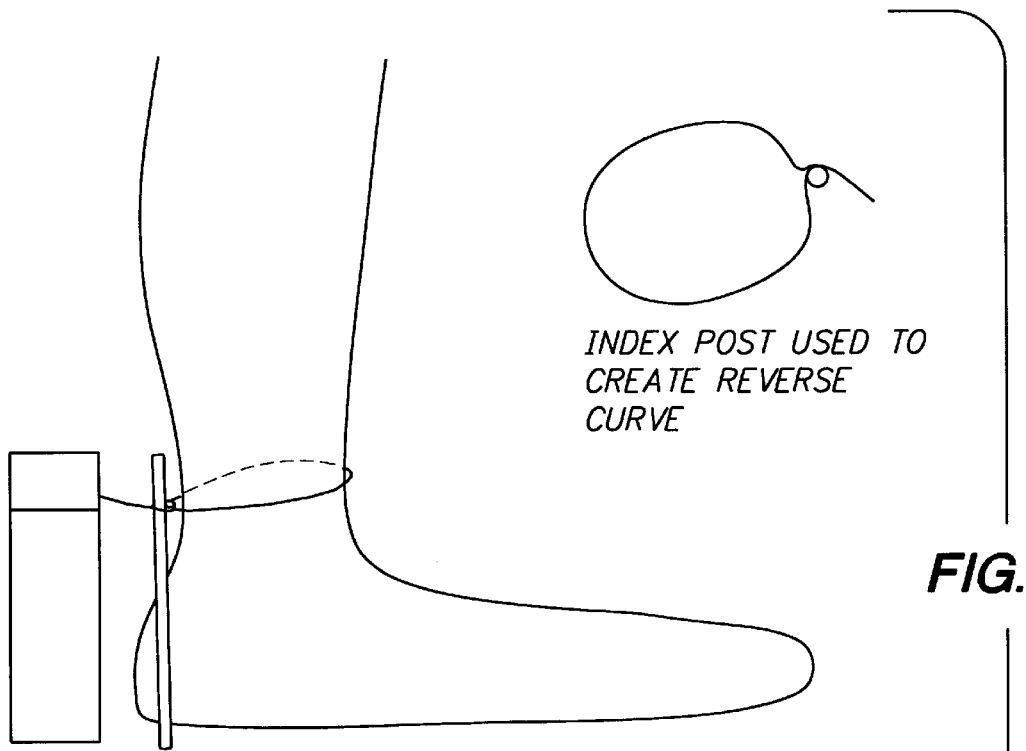
INDEX POST USED TO CREATE REVERSE CURVE
INDEX POST
ATTACHMENT CAN BE MADE TO CABEL ITSELF OR TO POST
FIG. 2
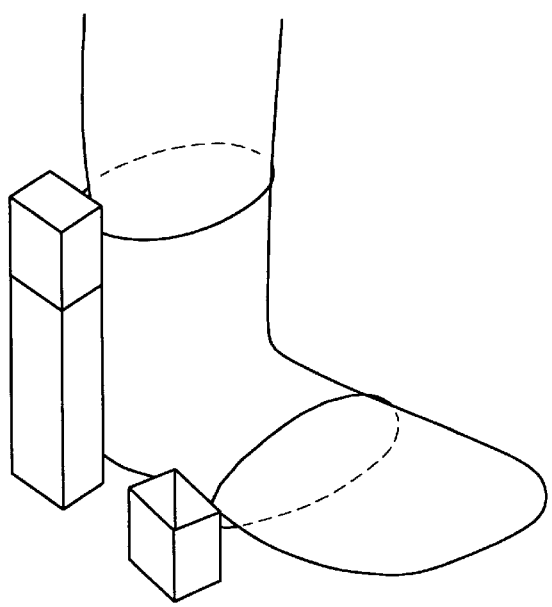
PREF. EMBODIMENT USES TWO MEASUREMENTS

METHOD FOR DETECTING EDEMA

TECHNICAL FIELD

The field of this invention is diseases characterized by edema.

BACKGROUND OF THE INVENTION

Edema is defined as the abnormal accumulation of fluid in connective tissue. Edema typically results from a combination of passive venous congestion and salt and water retention, and may be systemic or localized to a particular region of the body. Dependent edema, in which fluid accumulates in the tissues of the limbic extremities, e.g. ankle, foot and the like, is a physical manifestation of a number of different human disease conditions. Dependent edema first appears in the feet and ankles of the ambulatory patient, and in the posterior surface of the calves and skin overlying the sacrum in the bedridden patient. Disease conditions characterized by the presence of dependent edema include local venous or lymphatic obstruction, cirrhosis, hypoalbumenia, and congestive heart failure, particularly congestive hear failure associated with right-sided failure.

In congestive heart failure, the presence of edema in the lower extremities is valuable diagnostic marker for the presence of the disease. In addition to serving as a marker for the presence of congestive heart failure, the progression of the edemic state can be monitored over time and the progression of the edemic state related to the progression of the disease.

One way of detecting the presence of edema is to determine fluid volume change of the patient. A number of different technologies have been developed to identify the volume change, and include those based on the use of water or air-filled cuffs, mercury strain gauge, fiber optic strain gauge, and airborne ultrasound. Such technologies have principally been employed to measure venous blood flow and to sense the volume pulsations created by the heart.

In adults, edema is also detectable by the pitting method. In this method, a physician's thumb or finger is pressed into the patient's skin next to a bony surface (e.g., tibia, fibula, or sacrum). When the physician's finger is withdrawn, an indentation persists for a short time. The depth of the "pit" is estimated and generally recorded in millimeters, although subjective grading systems (e.g. "+++", etc.) have also been described. In general, the distribution of edema is also noted, as the amount of fluid is roughly proportional to the extent and the thickness of the pit.

Because dependent edema is a physical manifestation of a number of different disease conditions, the development of accurate methods for the detection of edema is of interest. Of particular interest is the development of methods which are sufficiently inexpensive and simple so as to be amenable to use in both conventional and out-patient health-care settings.

Relevant Literature

Scientific American Medicine (Dale & Freeman eds)1:II provides a review of congestive heart failure, physical manifestations and methods for the treatment thereof.

Lindahl & Omata, Med. Biol. Eng. Comput. (1995) 33:27–32 provide a description of methods of assessing edema.

SUMMARY OF THE INVENTION

Methods, and devices for use therein, for monitoring edema are provided. In the subject methods, one or more perimeters of a limbic extremity of a mammalian host are measured. Of particular interest is the use of a cable extension transducer to obtain the measured perimeter value. The measured distance is then related to the presence or absence of edema. The measurement may be repeated a number of times, so that the progression of the edemic state can be monitored. The subject methods find use in the diagnosis and management of a number of different diseases where edema is a physical manifestation, including local venous or lymphatic obstruction, cirrhosis, hypoalbuminemia and congestive heart failure, particularly right sided congestive heart failure.

BRIEF DESCRIPTION OF THE FIGURES

FIG. 2 depicts the measurement of a limb using a reference rod.

DESCRIPTION OF THE SPECIFIC EMBODIMENTS

Figure 1:
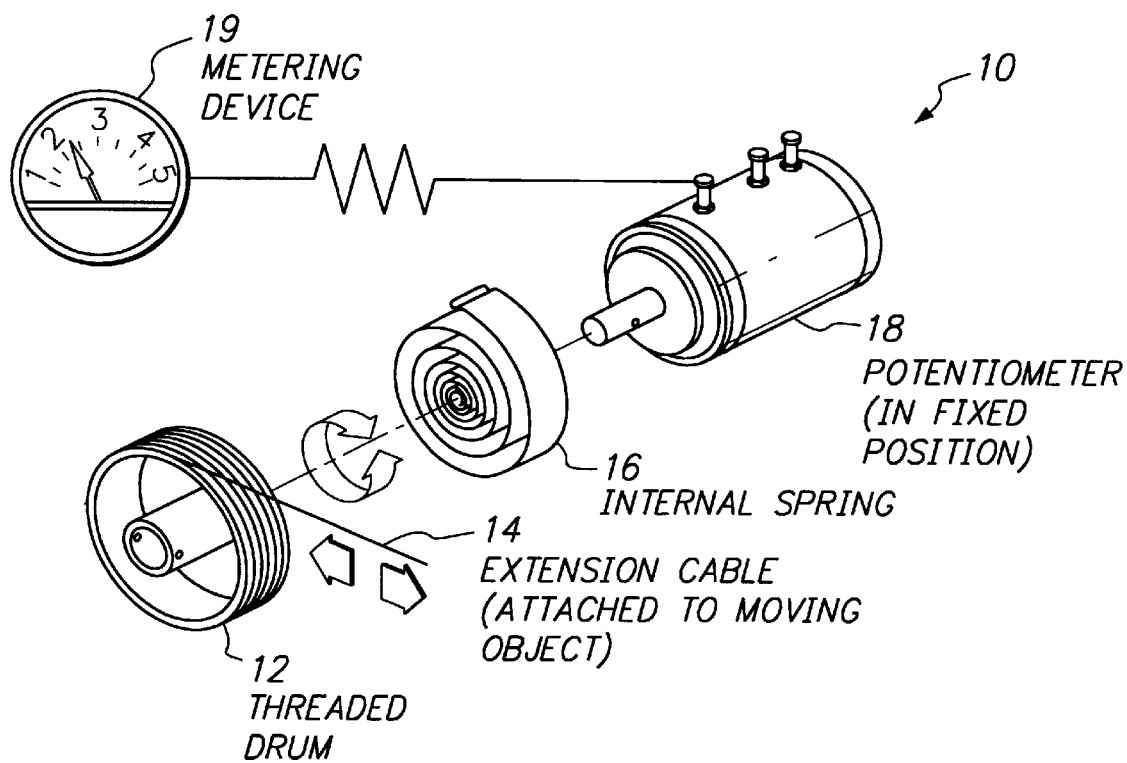
FIG. 1 provides an exploded view of a cable extension transducer suitable for use in the subject invention.

Methods and devices are provided for monitoring edema. In the subject methods, the perimeter of at least one limbic extremity, preferably an ankle or foot, of a mammalian host, is accurately measured. Of particular interest is the use of a cable extension transducer device to obtain the measured perimeter value. The measured value is then related to the presence or absence of edema. In the subject methods, the perimeter may be measured a plurality of times, usually according to a predetermined schedule, so that the progression of the edemic state may be monitored. The subject methods find use in the diagnosis and management of diseases characterized by the presence of edema, particularly right-sided congestive heart failure.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

The first step of the subject methods is to measure the perimeter of a limbic extremity of the mammalian host, e.g. human patient. In measuring the perimeter, the distance around a region of the limb, i.e. the circumference, is determined. Generally the limb that is measured is a lower extremity or region, portion or location thereof, where usually the perimeter of at least one of the ankle and foot are measured. In the subject methods, the perimeter of only a single region, portion or location of the limb may be measured, or the perimeter at a plurality of locations may be measured, where when a plurality of locations are measured, usually the number of different locations that are measured will not exceed three, and usually will not exceed two.

For measuring the perimeter, a measuring device that is capable of providing an accurate measurement of the limb perimeter is employed. Preferably the device is simple, inexpensive, and able to provide data that can readily be input into a microprocessor. Of particular interest in the subject invention is the use of cable extension transducer devices for perimeter measurement. Ideally, the transducer devices are easily handled, typically having a length ranging from 2.5 to 3.5 in, a height ranging from 1.5 to 2.0 in and a width ranging from 1.75 to 2.75 in. Preferably, the devices are also lightweight, having an weight that does not exceed 100 g and usually does not exceed 80 g.

A variety of cable extension transducer devices are known and suitable for use in the subject methods. Cable extension transducer devices are described in U.S. Pat. Nos. 5,236,144 and 5,560,118, the disclosures of which are herein incorporated by reference.

Cable extension transducer devices are available from a number of different commercial sources, including: Unimeasure (Corvalis, Oreg.); SpaceAge Control, Inc. (Palmdale, Calif.); Celesco Transducer Products, Inc. (Canoga Park, Calif.); Patriot Sensors & Controls Corporation (Simi Valley, Calif.); and the like.

Cable extension transducer devices suitable for use in the subject invention can be configured in a variety of different ways. In one suitable embodiment, the transducer comprises a cable extension attached to a rotary shaft that is, in turn, attached to a precision potentiometer. This embodiment is shown greater detail in FIG. 1. which provides an exploded view of such a device. In the device shown in FIG. 1, device 10 comprises a threaded drum 12 around which is wound an extension cable 14. The device further comprises an internal spring 16 and a potentiometer 18 and is connected to metering device 19. In this embodiment, the extent to which the cable is transduced to a resistance value, which value can then be correlated back to a length value. In an alternative embodiment, the cable extension is attached to a rotary shaft encoder and the device further comprises a digital counter that is capable of counting the pulses provided by the encoder. The extent to which the cable is extended during measurement is then transduced into a digital readout.

Cable extension transducer devices suitable for use should have cables fabricated from suitable flexible materials so that the cable can be snugly wrapped around the portion of the limb being measured in a manner where excessive compression of the flesh is avoided.

In using cable extension transducer devices to measure the perimeter of the limb, first a location of the lower extremity will be selected, e.g. the ankle, the foot and the like. The cable is then wrapped around the circumference of the limb at the location of measurement, with care taken to ensure the cable is sufficiently taut to eliminate any air spaces between the limb tissue and the cable, but not so excessively taut such that the cable compresses into, and depresses below, the surface of the flesh.

In using cable transducer devices for measuring the perimeter, it is preferable to base the perimeter value on the length of cable directly in contact with the tissue, i.e. to only use the cable distance beginning from the actual point of contact with the skin to the end of the cable and exclude that portion of the cable distance extending from the device to the skin. Put another way, the end of the cable that is wrapped around the limb should attach directly to the cable at the point where the cable initially contacts the skin from the device, and not at a region of the cable closer to the cable outlet of the device, since contacting at the latter region would result in the presence of an "air-gap" which would provide a potential source of error in measurement.

One way to ensure that the measured distance is derived directly from cable actually contacting the tissue surface is to use the device in conjunction with a reference rod or other device which allows for a "reverse curve" at the initial point of contact between the cable and the limb, as depicted in FIG. 2. In this embodiment, a reference rod is placed next to the limb tissue at the location where the perimeter is to be measured. Cable exiting the transducer device is first wrapped around the reference rod in a direction counter to the direction it then travels around the limb. By holding the transducer at a constant location relative to the limb, the cable distance between the transducer and the limb is then known and can be treated as a "zero shift" or offset in the measurement determination step.

Figure 3:
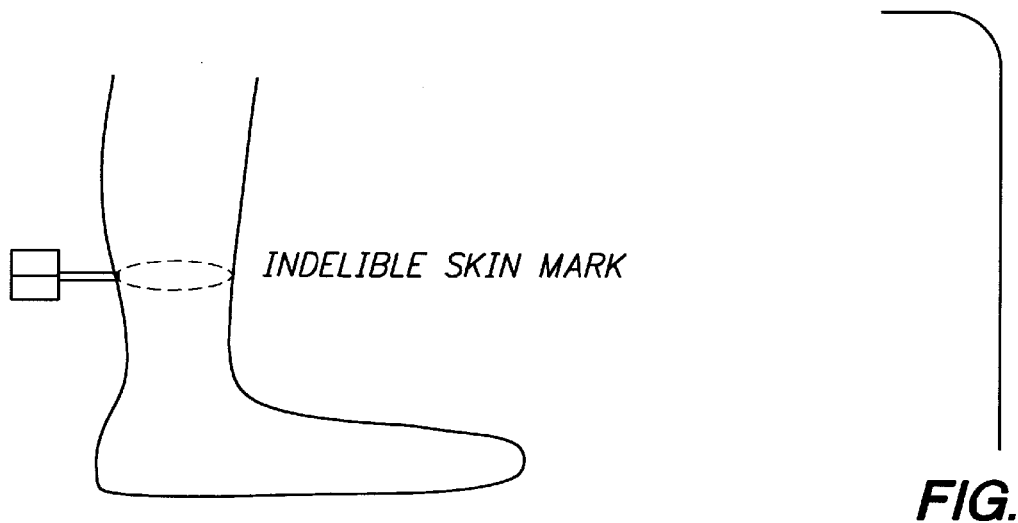
FIG. 3 depicts the measurement of a limb using a portable transducer fitted with a tube.
Figure 3:
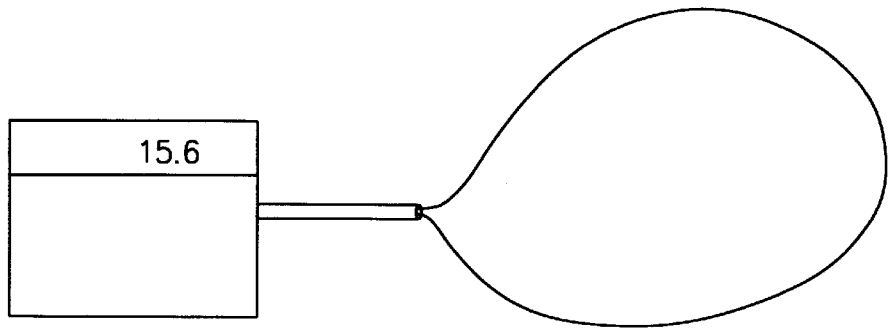

Instead of using a reference rod, the cable may extend from the transducer device through a tube, as shown in FIG. 3. In this embodiment, the cable extends from the device through a tube and then around the limb, not shown. The end of the cable is then attached to the point of the cable that first emerges from the tube at the point of contact with the skin.

In those embodiments of the invention where multiple measurements are taken of the same region over a period of time, e.g. days, weeks, months or longer, it is critical that the location that is measured be substantially the same for each measurement. One means of ensuring that substantially the same location is measured each time is to use a transducer device where the location of the transducer is fixed and constant relative to the limb being measured. For example, where the location to be measured is an ankle or foot, a device suitable for use will comprise, in addition to a fixed transducer, a means for ensuring that the foot is always positioned at the same place relative to the fixed transducer. Such means could be as simple as an reference mark, e.g. a foot outline, on a platform that indicates where the foot should be placed. Alternatively, the means could comprise ankle cups, gripping devices and the like, that more stably secure the limb in a fixed position relative to the transducer. Another means of ensuring that the same location is measured is to mark the region to be repeatedly measured with an at least a semi-permanent marking means, such as an indelible ink.

In some embodiments of the subject invention, it may be desirable to make two or more perimeter measurements at different locations. In such embodiments, one may use a portable transducer device which is not fixed at any particular location relative to the limb being measured. Alternatively, one may employ a fixed device comprising two or more transducers positioned at fixed locations relative to different locations of the limb. In yet a further embodiment, one could have a transducer device that comprises two or more cables.

The extent the cable is extended around the limb is then transduced into a perimeter value. The steps taken to transduce the cable extent into a perimeter value will depend on the particular transducer device employed. For example, with the resistance device depicted in FIG. 1, the extent to which the cable is extended around the limb is automatically transduced by the device into a certain resistance value. This resistance value can then be used as a perimeter value, or further transduced into actual distance units (or other convenient units) which can then serve as the perimeter value.

In the subject methods, the next step is to compare the perimeter value to a control value. The control value will be a value which corresponds to the perimeter of the limb at the location that is measured in the absence of the edemic state. Where possible to measure the limb in the absence of edema, such as in the case of pregnancy when the measurement can be made at an early time in anticipation of later indications of edema, then such non-edemic measurements can be used as a control value. Most often this is not possible as the desirability of edemic measurements is not apparent until the edema is already a problem. In this case the best indication of the non-edemic control value is simply the lowest value obtained from a series of perimeter measurements taken over a period of time. If a microprocessor or other computer device is available, then the recording and displaying of the measurements allows an instant graphic display of not only the measured amount of edema but, often more importantly, whether the condition is worsening or improving. The measured perimeter value and the control value will be compared and any difference will be identified.

The presence of a positive difference between the perimeter value and the control value is then correlated to the presence of swelling in the region of measurement and edema in the patient. Conversely, the absence of a difference or a negative difference may be related to the absence of the edemic state. Accordingly, the final step of the subject methods is to attribute the presence of a positive difference to the presence of edema in the patient.

The subject methods may be used to make multiple measurements over a given period of time so that the progression of the edemic state may be monitored. Where multiple measurements are made, the measurements will typically be made according to a schedule, where the measurements may be made hourly, daily, weekly, monthly and the like.

A microprocessor may be used in the conjunction with the subject methods. For example, the measured perimeter value may be input into a microprocessor device that then takes the data and performs the comparison with a predetermined control value and provides a readout of any difference. The microprocessor could also transmit the input data to a remote site for further processing and use. Such an embodiment finds use in applications were measurements are taken at sites remote to the medical personnel in charge of interpreting the results, such as in outpatient clinics, at the home and the like.

The subject methods find use with a variety of mammalian hosts where the detection of dependent edema is desired. Mammalian hosts with which the subject methods may find use include highly valuable, rare and exotic animals, domestic animals, such as livestock and pets, and humans.

Of particular interest is the use of the subject methods in the diagnosis and management of human diseases in which dependent edema is a physical manifestation, such as venous or lymphatic blockage, cirrhosis, hyperalbumenia and congestive heart failure, where congestive heart failure characterized by failure of the right ventricular, e.g. right-sided and biventricular heart failure, is of particular interest.

In using the subject methods in the diagnosis of congestive heart failure, the detection of edema by the subject methods is used as an indication of the presence of congestive heart failure, particularly right-sided or biventricular heart failure. In making such diagnoses, jugular venous distention will be also be detected, since the presence of both conditions can be used as assurance that the underlying disease condition is congestive heart failure, and not another disease characterized by the presence of dependent edema, such as local venous or lymphatic obstruction, cirrhosis or hypoalbumenia.

Also of particular interest is the use of the subject methods in the management of congestive heart failure. In managing congestive heart failure, a plurality of measurements will be taken according to a schedule and the progression the edemic state will be monitored. In this manner, the affect of various treatment methodologies on the symptoms associated with and/or the progression of the underlying disease can be assessed.

The following examples are offered by way of illustration and not by way of limitation.

EXPERIMENTAL

A. A sixty year old man with congestive heart failure resides at home with a care giver. A computerized telephonic monitoring system is installed which transmits information to a centralized nursing station. The system requires the patient to complete a daily monitoring cycle which includes answering questions on his general health, sleeping, appetite, and any unusual symptoms. As well, the patient stands on an electronic scale which records his weight, and while seated on a closed toilet seat or in a low chair places his foot on an indicated location on a flat plate attached to two cable transducers. One cable is secured around his instep, and one cable is secured around his lower leg. The patient presses a button to record the measurements and detaches the apparatus. At a later time, the computer system transmits the entire information set collected, including the edema measurements, to the central station. With an analysis of this daily information, a physician has early warning information, and can provide prompt care, avoiding acute episodes.

B. A number of patients in a general hospital are selected for edema monitoring for a variety of reasons. Once a day a nurse using a portable cable transducer monitor visits each patient. After entering each patient's number into the portable monitor, the nurse extends the cable and attaches it around the patient's lower leg at a premarked position, an allows the monitor to record the measurement. Upon the completion of her rounds the monitor is briefly attached to the hospital information system, which updates each patient's file with the measurement. The hospital information system provides the physician with a graphical display of the daily measurement results.

It is evident from the above results and discussion that improved methods for detecting dependent edema in a mammalian host are provided. Because the subject methods use relatively simple and inexpensive measurement devices, the methods are amenable for use in high volume situations and out patient settings by moderately skilled personnel, and therefore provide an attractive alternative to currently employed methods of detecting edema which are based on the detection of volume changes.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for detecting the presence of edema in a mammalian host, said method comprising:

measuring the perimeter value of at least one lower extremity selected from a group consisting of ankle and foot of said host; and relating the perimeter value to the presence of edema in said host;

whereby the presence of edema in said host is detected.

2. The method according to claim 1, wherein said relating step comprises comparing the measured perimeter value to a control value and attributing any difference in values to the presence or absence of edema.

3. A method for detecting the presence of edema in a human, said method comprising:

measuring the perimeter value of at least one lower extremity in said human;

comparing the measured perimeter value to a control value to obtain a difference; and attributing any difference to the presence or absence of edema in said human;

whereby the presence of edema in said human is detected.

4. The method according to claim 3, wherein said lower extremity is selected from the group consisting of foot and ankle.

5. The method according to claim 3, wherein said measuring step comprises using a cable extension transducer device.

6. The method according to claim 3, wherein said measured perimeter value is input into a microprocessor.

7. The method according to claim 3, wherein said measured perimeter value is transmitted to a site remote from the site where said measured perimeter value is measured.

8. The method according to claim 3, wherein said measured perimeter value is measured a plurality of times and the progression of said edema is monitored.

9. The method according to claim 8, wherein said detection of edema is used in at least one of the diagnosis and management of congestive heart failure.

10. A method for detecting the presence of edema in a patient suffering from congestive heart failure, said method comprising;

measuring the perimeter value of at least one lower extremity of said patient with a cable extension transducer, wherein said lower extremity is selected from the group consisting of foot and ankle;

comparing the measured perimeter value of said lower extremity to a control value and determining any difference;

attributing said difference to the presence or absence of edema in said patient;

whereby the presence of edema in said patient is detected.

11. The method according to claim 10, wherein said congestive heart failure is right-sided congestive heart failure.

12. The method according to claim 10, wherein said method is used in the diagnosis of said congestive heart failure.

13. The method according to claim 10, wherein said method is used in the management of said congestive heart failure.

14. The method according to claim 13, wherein said measuring is repeated a plurality of times and the progression of said edema is monitored.

15. The method according to claim 10, wherein said measured perimeter value is input into a microprocessor.

16. The method according to claim 10, wherein said measured perimeter value is transmitted to a remote site.

17. The method according to claim 14, wherein said repeated measurements are taken according to a schedule.

* * * * *